(12) United States Patent
Distefano et al.

(10) Patent No.: US 10,940,106 B2
(45) Date of Patent: Mar. 9, 2021

(54) BIODEGRADABLE COPOLYMERS FOR COSMETIC USE

(71) Applicant: INTERCOS S.p.A., Milan (IT)

(72) Inventors: Gaetano Distefano, Bergamo (IT); Patrizia Valsesia, Calco LC (IT); Claudia Crusco, Concorezzo MB (IT); Sara Bettinelli, Parabiago MI (IT); Gabriele Depta, Monza (IT)

(73) Assignee: INTERCOS S.P.A., Milan (IT)

( * ) Notice: Subject to any disclaimer, the term of this patent is extended or adjusted under 35 U.S.C. 154(b) by 0 days.

(21) Appl. No.: 16/097,710

(22) PCT Filed: May 5, 2017

(86) PCT No.: PCT/IB2017/052620
§ 371 (c)(1),
(2) Date: Oct. 30, 2018

(87) PCT Pub. No.: WO2017/191603
PCT Pub. Date: Nov. 9, 2017

(65) Prior Publication Data
US 2019/0159999 A1    May 30, 2019

(30) Foreign Application Priority Data

May 5, 2016  (IT) .................. 102016000046513

(51) Int. Cl.
*A61K 8/892* (2006.01)
*A61Q 1/06* (2006.01)
*A61Q 1/10* (2006.01)
*A61Q 1/12* (2006.01)
*A61Q 3/00* (2006.01)
*A61Q 3/02* (2006.01)
*C08G 77/38* (2006.01)

(52) U.S. Cl.
CPC ............... *A61K 8/892* (2013.01); *A61Q 1/06* (2013.01); *A61Q 1/10* (2013.01); *A61Q 1/12* (2013.01); *A61Q 3/00* (2013.01); *A61Q 3/02* (2013.01); *C08G 77/38* (2013.01)

(58) Field of Classification Search
None
See application file for complete search history.

(56) References Cited

U.S. PATENT DOCUMENTS

| 5,194,473 A | 3/1993 | Shinoda et al. |
| 2004/0146540 A1 | 7/2004 | Ueda |
| 2010/0099841 A1 | 4/2010 | Lin |

FOREIGN PATENT DOCUMENTS

| EP | 0 399 827 | 11/1990 |
| EP | 1 400 233 | 3/2004 |

OTHER PUBLICATIONS

International Search Report dated Aug. 21, 2017 in International Application No. PCT/IB2017/052620.
International Preliminary Report on Patentability dated Aug. 21, 2017 in International Application No. PCT/IB2017/052620.
Hans R. Kricheldorf et al., "Stereocomplexes of A-B-A Triblock Copolymers Based on Poly(L-Lactide) and Poly(D-Lactide) A Blocks", Macromolecules, vol. 38, No. 16, Aug. 1, 2005, XP055093007.
Paul Böhm: "Functional Silicones and Silicone-Containing Block Copolymers Dissertation Zur Erlangung des Grades "Doktor De Naturwissenschaften" Table of Contents", Aug. 1, 2012, pp. 1-139, XP055313814, Mainz Retrieved from the Internet: URL:http://ubm.opus.hbz-nrw.de/volltexte/2012/3194/pdf/doc.pclf [retrieved on Oct. 25, 2016].
Marc D. Rodwogin et al., "Polylactide-Poly(dimethylsiloxane)-Polyactide Triblock Copolymers as Multifunctional Materials for Nanolithographic Applications", Acs Nano, vol. 4, no. 2, Feb. 23, 2010, pp. 725-732, XP055344874.

*Primary Examiner* — Bong-Sook Baek
(74) *Attorney, Agent, or Firm* — Wenderoth, Lind & Ponack, L.L.P.

(57) ABSTRACT

Biodegradable copolymers for cosmetic use are described, obtained by reaction between lactide and a silicone initiator. Said copolymers are used for the preparation of cosmetic products such as lipsticks, facial cosmetic powders, creams, eyeliners, eye shadows.

9 Claims, No Drawings

BIODEGRADABLE COPOLYMERS FOR COSMETIC USE

The present invention relates to the preparation of biodegradable copolymers for cosmetic use.

The use of biodegradable materials is one of the most effective approaches to contribute to the resolution of environmental pollution problems that arise, among other things, from the huge use of petrochemical plastic materials.

The raw materials used in cosmetics can have a petrochemical, synthetic, animal or vegetable origin. Some petrochemical raw materials will even be banned in some States by 2020 (e.g. in California, a State in the vanguard as regards legislation in the U.S.) due to the pollution caused to the aquifers. These non-biodegradable materials escape from sewage treatment plants and are released into the environment with threats to aquatic species.

The most obvious green alternative to these types of cosmetic raw materials undoubtedly are biopolymers, which combine the plant origin of the starting raw materials (biomass fermentation) with the versatility of synthesis chemistry. For this reason, it is strategic to address the innovation effort towards raw materials of plant origin, which are varied through chemical synthesis, possibly applying the principles of "Green Chemistry".

In this regard, more and more attention is being paid to the study and modification of polylactic acid (hereinafter "PLA") which is the most promising biopolymer to date due to its complete biodegradability, good thermal processability, renewability, good mechanical performance, etc.

This polymer has been extensively studied over the last 25 years and scientific and technical knowledge has enabled the emergence of the first industrial applications to date. In fact, PLA has already found extensive use in a variety of fields, and in particular in the biomedical sector: due to its biocompatibility and biodegradability, it has been found to be effective in the manufacture of medical devices for the controlled release of drugs, plaques and nails for bone fixation, surgical sutures which, in contact with the body, have shown a decrease in inflammatory reactions and infections. Another great search front is packaging: packaging in fact has a considerable environmental impact and therefore it is natural to use compostable and biodegradable materials to reduce the impact thereof.

PLA has so far found cosmetic use only in the form of powder with texturizing purpose in decorative cosmetics and as a scrub in rinsing products. PLA cosmetic powders were marketed by Honeywell International, Inc. under the trade name of Asensa and by Daito Kasei Kogyo Co., Ltd. under the trade name of Ecobeads.

To date, the most effective polymerization method at industrial level for the synthesis of PLAs with high molecular weight envisages a ring opening polymerization (hereafter "ROP") starting from the cyclic dimer of lactic acid (lactide).

The synthesis of biopolymers containing PLA through ROP is well known in the literature and a lot of scientific evidence has described and analyzed various processes for obtaining said biopolymers or co-polymers containing PLA. It is also known in the art that polymerization of lactate by ROP occurs efficiently in the presence of organometallic catalysts (e.g. tin(II) ethylhexanoate) at high temperature and with the aid of alcoholic co-initiators.

For example, Hazer et al., (*Journal of Polymers and the Environment,* 2012) describes the synthesis of PLA and polydimethylsiloxane copolymers (hereafter "PDMS"). Said copolymers are obtained by trans-esterification reaction between poly(dimethyl siloxane)bis(2-aminopropyl ether) with PLA, in a chloroform solution and in the presence of stannous octoate.

Lee W K et al. (*Composite Interfaces,* 2006) describes the synthesis of polyester and polydimethylsiloxane copolymers by ROP initiated by alcoholic co-initiators.

Nagarajan S. et al. (*Macromolecules* 2015) describes cold crystallization of copolymers of poly(L-lactide-b-dimethylsiloxane-b-L-Lactide) by ROP of L-lactide using bis(hydroxyalkyl)-terminated PDMS as macroinitiator.

Hans R. Kricheldorf et al, (Macromolecules 2005) describes the synthesis of copolymers of poly-lactide and PDMS. The copolymers are produced by the reaction of lactide and $\alpha,\omega$-bis(3-hydroxypropyl) PDMS.

Paul Böhm (Dissertation Zur Erlangung des Grades "Doktor der Naturwissenschaften", 2012) describes a method of ROP of lactide in the presence of PDMS as macroinitiator and a catalyst.

EP0399827A2 describes a polyester compound suitable for cosmetic uses obtained by ROP of lactide in the presence of a silicone.

EP1400233A1 describes the use of PLA as a primary component of cosmetic products.

US2010/099841A1 describes an amorphous biodegradable PLA extracted from plants.

The above reactions take place at high temperatures even in the presence of alcoholic initiators or co-initiators, said reactions allow to obtain high molecular weight copolymers with chemical and physical properties that do not allow a wide use thereof in cosmetics.

The object of the present invention is to obtain biodegradable copolymers for cosmetic use with a wide possibility of use in the cosmetic field.

Another object is to obtain biodegradable copolymers whose fluidity can be changed only by varying the proportion of the moles of the starting reagents.

A further object is to obtain biodegradable copolymers for cosmetic use with a low environmental impact and unprecedented textures.

According to the invention, such objects are achieved with biodegradable copolymers for cosmetic use as described in claim 1.

The object of the present invention is a method for the preparation of biodegradable block copolymers "A-B-A", consisting of a central polysiloxane block (PDMS) called "B", and two symmetrical PLA blocks, called "A", PLA-PDMS-PLA and their use in cosmetic products. The applicant's research has in fact shown that the properties of these materials vary continuously and predictably with the variation of the PLA/PDMS ratio and the molecular weights of the two constituent blocks A and B.

Via chemical synthesis it is therefore possible to access a series of compatible chemical compounds with different consistencies, from fluid materials to pastes, to plastic materials, up to hard solid materials. Such a wealth of behaviors can be suitably used in the formulation of new cosmetic products which have a reduced environmental impact and unprecedented textures.

It is known in the art that polymerization of lactate by ROP occurs efficiently in the presence of organometallic catalysts (e.g. tin(II) ethylhexanoate) at high temperature and with the aid of alcoholic co-initiators.

In the present invention, in lieu of low molecular weight alcohols, a linear or branched silicone macroinitiator with alcoholic functionality in $\alpha$ and $\omega$ terminal position is used to start the chain reaction and symmetrically add the PLA terminal blocks to the central polysiloxane one.

Depending on the amount of polymerized lactide, final molecular weights may be reached ranging from 2500 Da to more than 50 kDa and therefore materials with markedly different features.

These and other features of the present invention will be apparent from the following detailed description and embodiment examples thereof.

Hereinafter, the PLA-PDMS copolymers obtained will be named with the fantasy name "Diplathicone".
The following Table 1 gives an indication of the features that can be obtained by varying the proportions between silicone segment and PLA segment.

TABLE 1

Physical and chemical properties of some PLA-PDMS-PLA block copolymers

| Name | Lactide % by weight | 5562 Carbinol Fluid % by weight | Appearance at 25° C. | Viscosity/ cP | Mw GPC/ Da |
|---|---|---|---|---|---|
| DIPLATHICONE LV | 20 | 80 | Clear fluid | 350 | 3000 |

TABLE 1-continued

Physical and chemical properties of some PLA-PDMS-PLA block copolymers

| Name | Lactide % by weight | 5562 Carbinol Fluid % by weight | Appearance at 25° C. | Viscosity/ cP | Mw GPC/ Da |
|---|---|---|---|---|---|
| DIPLATHICONE MV | 40 | 60 | Milky fluid | 15000 | 3500 |
| DIPLATHICONE HV | 50.0 | 50.0 | Milky paste | >$10^5$ | 4500 |
| DIPLATHICONE V-HV | 75.0 | 25.0 | Malleable solid | n.a. | 6000 |
| DIPLATHICONE POWDER | 95.0 | 5.0 | Powder | n.a. | 20000 |

The opportunity is even more interesting in view of the fact that, although such materials are described in scientific and patent literature, their use is not described or protected in cosmetics.

In this regard, it is noted that the CTFA dictionary only reports the following materials based on building blocks of lactic acid.

TABLE 2

List of raw materials recorded in the cosmetic dictionary containing lactic acid derivatives

| CTFA name | CTFA definition | Tradename (manufacturer) |
|---|---|---|
| Polylactide | Polylactic Acid is a polymer of Lactic Acid (q.v.). | Cyclic Poly Lactate (CPL) (Lactive Japan Inc.) Ecoscrub 20PC (Micro Powders, Inc.) Flo-Beads BF (Sumitomo Seika Chemicals Co., Ltd.) FLO-BEADS BL (Sumitomo Seika Chemicals Co., Ltd.) Flo-Beads BR (Sumitomo Seika Chemicals Co., Ltd.) Lacea (Kane Kogyo Co., Ltd.) PLLA-MS (Samkyung Costech Co., Ltd.) Purasorb OL (Purac Biochem BV) |
| Lactide/Succinimide Copolymer" | Lactide/Succinimide Copolymer is the copolymer formed by the reaction of Aspartic Acid (q.v.) with lactide. | Aspartic Acid/Lactic Acid Copolymer (Mitsui-Chemicals, Inc.) |
| PEG-180 Bispolylactide | PEG-180 Bispolylactide is the block copolymer that conforms generally to the formula: 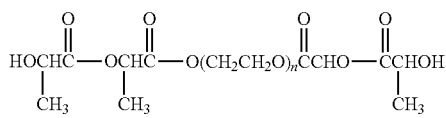 where n has an average value of 180. | mnemoCos 9000 L (mNemoscience GmbH) mnemoCos 9000 S (mNemoscience GmbH) |
| Calcium Stearoyl Lactylate | Calcium Stearoyl Lactylate is the calcium salt of the stearic acid ester of lactyl lactate. It conforms to the formula: 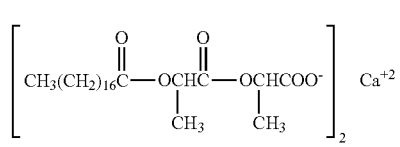 | n.a. |

TABLE 2-continued

List of raw materials recorded in the cosmetic dictionary containing lactic acid derivatives

| CTFA name | CTFA definition | Tradename (manufacturer) |
|---|---|---|
| Ethyl Lactyl Retinoate | Ethyl Lactyl Retinoate is the organic compound that conforms to the formula: $$\text{(structure of ethyl lactyl retinoate with cyclohexenyl polyene chain and }-C(=O)OCH(CH_3)C(=O)OCH_2CH_3\text{ group)}$$ | Lactic Retinoic Double Conjugate Ester (Pharma Cosmetix Research L.L.C.) |
| Lauroyl Lactylic Acid | Lauroyl Lactylic Acid is the organic compound that conforms to the formula: $$CH_3(CH_2)_{10}\overset{O}{\underset{}{C}}-OCH(CH_3)\overset{O}{\underset{}{C}}-OCH(CH_3)COOH$$ | n.a. |
| Lauryl Lactyl Lactate | Lauryl Lactyl Lactate is the organic compound that conforms to the formula: $$HOCH(CH_3)\overset{O}{\underset{}{C}}-OCH(CH_3)\overset{O}{\underset{}{C}}-O(CH_2)_{11}CH_3$$ | Stepan-Mild L3 (Stepan Company) |
| Myristoyl Lactylic Acid | Myristoyl Lactylic Acid is the organic compound that conforms to the formula: $$CH_3(CH_2)_{12}\overset{O}{\underset{}{C}}-OCH(CH_3)\overset{O}{\underset{}{C}}-OCH(CH_3)COOH$$ | n.a. |
| Sodium Behenoyl Lactylate | Sodium Behenoyl Lactylate is the sodium salt of the behenic acid ester of lactyl lactate. It conforms to the formula: $$CH_3(CH_2)_{20}\overset{O}{\underset{}{C}}-OCH(CH_3)\overset{O}{\underset{}{C}}-OCH(CH_3)COONa$$ | Pationic SBL (Rita Corporation) |
| Sodium Caproyl Lactylate | Sodium Caproyl Lactylate is the sodium salt of the capryl ester of lactyl lactate. It conforms generally to the formula: $$CH_3(CH_2)_{8}\overset{O}{\underset{}{C}}-OCH(CH_3)\overset{O}{\underset{}{C}}-OCH(CH_3)COONa$$ | Capmul S 10 L (Abitec Corporation) Pationic 122A (Rita Corporation) |

TABLE 2-continued

List of raw materials recorded in the cosmetic dictionary containing lactic acid derivatives

| CTFA name | CTFA definition | Tradename (manufacturer) |
|---|---|---|
| Sodium Caproyl/Lauroyl Lactylate | Sodium Caproyl/Lauroyl Lactylate is the organic compound that conforms generally to the formula:<br><br>$$\underset{RC}{\overset{O}{\|}}-O\underset{\underset{CH_3}{\|}}{CH}\overset{O}{\overset{\|}{C}}-O\underset{\underset{CH_3}{\|}}{CH}COONa$$<br><br>where RCO— represents a mixture of capric and lauric acid groups. | Dermosoft Decalact (Dr. Straetmans Gmbh) |
| Sodium Cocoyl Lactylate | Sodium Cocoyl Lactylate is the sodium salt of the coconut acid ester of lactyl lactate. It conforms to the formula:<br><br>$$\underset{RC}{\overset{O}{\|}}-O\underset{\underset{CH_3}{\|}}{CH}\overset{O}{\overset{\|}{C}}-O\underset{\underset{CH_3}{\|}}{CH}COONa$$<br><br>where RCO— represents the fatty acids derived from coconut oil. | Pationic SCL (Rita Corporation) |
| Sodium Isostearoyl Lactylate | Sodium Isostearoyl Lactylate is the sodium salt of the isostearic acid ester of lactyl lactate. It conforms to the formula:<br><br>$$\underset{C_{17}H_{35}C}{\overset{O}{\|}}-O\underset{\underset{CH_3}{\|}}{CH}\overset{O}{\overset{\|}{C}}-O\underset{\underset{CH_3}{\|}}{CH}COONa$$ | Oleester ISL (Sino Lion (USA) Ltd.)<br>Pationic ISL (Rita Corporation) |
| Sodium Lauroyl Lactylate | Sodium Lauroyl Lactylate is the sodium salt of the lauric acid ester of lactyl lactate. It conforms to the formula:<br><br>$$\underset{CH_3(CH_2)_{10}C}{\overset{O}{\|}}-O\underset{\underset{CH_3}{\|}}{CH}\overset{O}{\overset{\|}{C}}-O\underset{\underset{CH_3}{\|}}{CH}COONa$$ | Capmul S12L (Abitec Corporation)<br>Dermosoft SLL (Dr. Straetmans)<br>Pationic 138C (Rita Corporation) |
| Sodium Oleoyl Lactylate | Sodium Oleoyl Lactylate is the sodium salt of the oleic acid ester of lactyl lactate. It conforms to the formula:<br><br>$$\underset{CH=CH(CH_2)_7C}{\overset{(CH_2)_7CH_3}{\|}}\overset{O}{\overset{\|}{}}-O\underset{\underset{CH_3}{\|}}{CH}\overset{O}{\overset{\|}{C}}-O\underset{\underset{CH_3}{\|}}{CH}COONa$$ | n.a. |
| Sodium Stearoyl Lactylate | Sodium Stearoyl Lactylate is the sodium salt of the stearic acid ester of lactyl lactate. It conforms to the formula:<br><br>$$\underset{CH_3(CH_2)_{16}C}{\overset{O}{\|}}-O\underset{\underset{CH_3}{\|}}{CH}\overset{O}{\overset{\|}{C}}-O\underset{\underset{CH_3}{\|}}{CH}COONa$$ | AEC Sodium Stearoyl Lactylate (A & E Connock (Perfumery & Cosmetics) Ltd.)<br>Akoline SL (AarhusKarlshamn Sweden AB)<br>Capmul S18L (Abitec Corporation)<br>Pationic SSL (Rita Corporation)<br>Radiamuls 2990K (Oleon NV) |

TABLE 2-continued

List of raw materials recorded in the cosmetic dictionary containing lactic acid derivatives

| CTFA name | CTFA definition | Tradename (manufacturer) |
|---|---|---|
| Stearoyl Lactylic Acid | Stearoyl Lactylic Acid is the ester of stearic acid and lactyl lactate. It conforms to the formula: $$CH_3(CH_2)_{16}\overset{O}{\underset{\|}{C}}-O\underset{\underset{CH_3}{\|}}{C}H-O\underset{\underset{CH_3}{\|}}{C}HCOOH$$ | n.a. |
| TEA-Lauroyl Lactylate | TEA-Lauroyl Lactylate is the triethanolamine salt of the lauric acid ester of lactyl lactate. It conforms to the formula: $$CH_3(CH_2)_{10}\overset{O}{\underset{\|}{C}}-O\underset{\underset{CH_3}{\|}}{C}H-O\underset{\underset{COOH}{\|}}{C}HCH_3-N(CH_2CH_2OH)_3$$ | n.a. |

PDMS has high oxygen and water vapor permeability and is biocompatible, making the block copolymer, which is formed by the reaction with lactide, highly biocompatible and therefore of great importance to many fields, including cosmetics.

The possibility to modulate the fluidity of a cosmetic raw material obtained as described above, without changing the chemical composition but only the ratio in moles between the silicone component and the starting lactide, allows to obtain a wide family of cosmetic raw materials that can then be used in all types of cosmetics: face products (concealer, foundation, tinted creams, . . . ), lip products (lipsticks, lip balms, . . . ), eye decoration products (compact powders, fluids, . . . ), hair products, nail care and decoration products in all their physical forms (solid, liquid, gels or pastes).

More specifically, the reaction is conducted by reacting at least one linear and branched silicone initiator with at least one alcoholic functionality in α and ω) terminal position, for example a cosmetic bis-hydroxyterminated dimethicone that is selected from the group comprising Carbinol bis-hydroxy-terminated Polydimethylsiloxanes Baysilone OF OH 702 E (Momentive Performance Materials), Dow Corning 5562 Carbinol Fluid (Dow Corning Corporation), Emulsil S-362 (Innospec Performance Chemicals), Carbinol bis-hydroxy-terminated Polydimethylsiloxanes: DMS-C15, DMS-C16, DMS-C21, DMS-C23, DBE-C25, DBL-C31, DBP-C22 (Gelest), MonoCarbinol terminated Polydimethylsiloxanes: MCR-C12, MCR-C13, MCR-C18, MCR-C22 (Gelest), MonoDiCarbinol terminated Polydimethylsiloxanes: MCR-C61, MCR-C62 (Gelest), Linear and branched Hydroxy Functional Pre-Polymers: Silmer OH A0, Silmer OH C50, Silmer OH J10, Silmer OH Di-10, Silmer OH Di-50, Fluorosil OH C7-F (Siltech) with the lactide, L-lactide, D-lactide or LD-lactide, for example L-lactide (e.g. Puralact (Corbion)).

Preferably, said silicone initiator is Carbinol bis-hydroxy-terminated Polydimethylsiloxanes Baysilone OF OH 702 E (Momentive Performance Materials) or Dow Corning 5562 Carbinol Fluid (Dow Corning Corporation).

Preferably, said silicone initiator is hydroxyethoxypropyl dimethicone, even more preferably bis-hydroxyethoxypropyl dimethicone.

Said silicone initiator has a molecular weight greater than 1800 Da, preferably greater than 2000 Da, even more preferably between 2000 Da and 12000 Da.

Ring opening polymerization requires a catalyst that can be selected from zinc compounds such as zinc lactate, zinc(II) 2-ethylhexanoate, zinc stearate and tin compounds, such as tin octoate (tin(II)-2-ethylhexanoate) or tin alkoxides, or 4-(Dimethylamino)pyridine N-heterocyclic carbenes, 1,3-bis-(2,4,6-trimethylphenyeimidazol-2-ylideneN-heterocyclic carbenes, 1,3-bis-(2,4,6-trimethylphenyl) imidazolinium chloride Na salt of 2,6-di-tert-butyl-4-methylphenol, Tin(II) 2-ethylhexanoate.

The lactide, preferably L-lactide and the silicone initiator are added with different percentages by weight. The lactide will have a concentration by weight of between 10% and 95%. The silicone initiator will have a concentration by weight of between 5% and 90%. The catalyst will have a concentration by weight of between 0.005% and 0.02%.

At the end of the reaction between the lactide and the silicone initiator, biodegradable copolymers can be obtained having different chemical and physical properties, such as molecular weight, viscosity and density. These copolymers can take a clear fluid consistency at room temperature, or a milky fluid, or a paste, or even a solid.

Biodegradable copolymers have a molecular weight of between 2000 Da and 30 kDa, preferably between 2500 Da and 25 kDa, even more preferably between 3000 Da and 20 kDa.

Moreover, said copolymers have a Brookfield viscosity v of between 250 cP and 190000 cP and a density of between 1 g/cm$^3$ and 1.50 g/cm$^3$ at 25° C., preferably between 1.10 g/cm$^3$ and 1.20 g/cm$^3$, even more preferably between 1.03 g/cm$^3$ and 1.06 g/cm$^3$ at 25° C.

In a first embodiment in the presence of a catalyst, the lactide and the silicone initiator are made to react with a lactide concentration of between 10% and 20% by weight and a silicone initiator concentration of between 80% and 90% by weight. The copolymers obtained from said reaction will have a fluid consistency at room temperature, with a molecular weight Mw of between 1500 Da and 4500 Da, preferably between 2000 Da and 4000 Da, even more preferably between 2500 Da and 3500 Da, a Brookfield viscosity v of between 250 Cp and 20000 Cp, preferably between 300 Cp and 17500 Cp, even more preferably between 350 Cp and 15000 Cp, and a density at 25° C. of between 1 g/cm$^3$ and 1.50 g/cm$^3$, preferably between 1.10 g/cm$^3$ and 1.20 g/cm$^3$, even more preferably between 1.03 g/cm$^3$ and 1.06 g/cm$^3$.

In a second embodiment in the presence of a catalyst, the lactide and the silicone initiator are made to react with a lactide concentration of between 40% and 60% by weight and a silicone initiator concentration of between 40% and 70% by weight, preferably between 50% and 60% by weight. The copolymers obtained from said reaction will have the consistency of a paste at room temperature, with a molecular weight Mw of between 3500 Da and 6500 Da, preferably between 4000 Da and 6000 Da, even more preferably between 4500 Da and 5500 Da, a Brookfield viscosity v of between 130000 Cp and 190000 Cp, preferably between 140000 Cp and 180000 Cp, even more preferably between 150000 Cp and 170000 Cp. The resulting products do not have a melting/crystallization point detectable with standard techniques, such as differential scanning calorimetry, in the range in which the PLA has a melting/crystallization point of between 150° C. and 180° C.

In a third embodiment in the presence of a catalyst, the lactide and the silicone initiator are made to react with a lactide concentration of between 75% and 95% by weight and a silicone initiator concentration of between 5% and 25% by weight. The copolymers obtained from said reaction will have a solid consistency at room temperature, with a molecular weight Mw of between 4000 Da and 22000 Da, preferably between 5000 Da and 21000 Da, even more preferably between 6000 Da and 20000 Da, and a glass transition temperature Tg of between 20° C. and 60° C., preferably between 25° C. and 50° C., even more preferably between 28° C. and 48° C. Moreover, said solids will have a melting temperature of between 130° C. and 190° C., preferably between 140° C. and 180° C., even more preferably between 150° C. and 170° C. The resulting products do not have a melting/crystallization point detectable with standard techniques, such as differential scanning calorimetry, in the range in which the PLA has a melting/crystallization point of between 150° C. and 180° C.

The following examples are intended to clarify the present invention without limiting it in any way.

EXAMPLE 1

Synthesis of Diplathicone LV

To a 2 L five-neck glass jacketed reactor (mechanical stirring, downpipe, thermometer, nitrogen inlet and neck for adding reagents) are added 200 g L-lactide, 800 g Dimethicone bis-hydroxyterminated (Bis-hydroxyethoxypropyl Dimethicone, DC 5562 Carbinol Fluid) and 0.05 g tin(II) 2-ethylhexanoate. After flushing dry nitrogen for one hour, the internal temperature is brought to 140° C. and allowed to react to complete depletion of lactide, controlled by infrared spectroscopy. At the end of the reaction, the internal temperature is brought to 30° C. and a clear fluid is discharged, having a molecular weight GPC Mw=3000 Da, Brookfield viscosity v=350 cP and density d=1.03 g/cm3 at 25° C.

EXAMPLE 2

Synthesis of Diplathicone MV

To a 2 L five-neck glass jacketed reactor (mechanical stirring, downpipe, thermometer, nitrogen inlet and neck for adding reagents) are added 400 g L-lactide, 600 g Dimethicone bis-hydroxyterminated (Bis-hydroxyethoxypropyl Dimethicone, DC 5562 Carbinol Fluid) and 0.1 g tin(II) 2-ethylhexanoate. After flushing dry nitrogen for one hour, the internal temperature is brought to 140° C. and allowed to react to complete depletion of lactide, controlled by infrared spectroscopy. At the end of the reaction, the internal temperature is brought to 30° C. and a milky fluid is discharged, having a molecular weight GPC Mw=3500 Da, Brookfield viscosity v=15000 cP and density d=1.06 g/cm3 at 25° C.

EXAMPLE 3

Synthesis of Diplathicone HV

To a 2 L five-neck glass jacketed reactor (mechanical stirring, downpipe, thermometer, nitrogen inlet and neck for adding reagents) are added 500 g L-lactide, 500 g Dimethicone bis-hydroxyterminated (Bis-hydroxyethoxypropyl Dimethicone, DC 5562 Carbinol Fluid) and 0.15 g tin(II) 2-ethylhexanoate. After flushing dry nitrogen for one hour, the internal temperature is brought to 160° C. and allowed to react to complete depletion of lactide, controlled by infrared spectroscopy. At the end of the reaction, the temperature is lowered to 80° C. and a milky fluid is discharged that at room temperature takes the consistency of a translucent viscous paste. The material has a molecular weight GPC Mw=4500 Da, Brookfield viscosity v=150000 cP at 50° C.

EXAMPLE 4

Synthesis of Diplathicone V-HV

To a 2 L five-neck glass jacketed reactor (mechanical stirring, downpipe, thermometer, nitrogen inlet and neck for adding reagents) are added 750 g L-lactide, 250 g Dimethicone bis-hydroxyterminated (Bis-hydroxyethoxypropyl Dimethicone, DC 5562 Carbinol Fluid) and 0.2 g tin(II) 2-ethylhexanoate. After flushing dry nitrogen for one hour, the internal temperature is brought to 160° C. and allowed to react to complete depletion of lactide, controlled by infrared spectroscopy. At the end of the reaction, the temperature is lowered to 130° C. and a viscous fluid is discharged that at room temperature takes the consistency of a weakly yellow glassy and transparent solid. The material has a molecular weight GPC Mw=6000 Da and glass transition temperature Tg of between 28 and 30° C.

EXAMPLE 5

Synthesis of Diplathicone Powder

To a 2 L five-neck glass jacketed reactor (mechanical stirring, downpipe, thermometer, nitrogen inlet and neck for adding reagents) are added 950 g L-lactide, 50 g Dimethicone bis-hydroxyterminated (Bis-hydroxyethoxypropyl Dimethicone, DC 5562 Carbinol Fluid) and 0.2 g tin(II) 2-ethylhexanoate. After flushing dry nitrogen for one hour, the internal temperature is brought to 160° C. and allowed to react to complete depletion of lactide, controlled by infrared spectroscopy. At the end of the reaction, the temperature is lowered to 130° C. and a viscous fluid is discharged that at room temperature takes the consistency of a semicrystalline white solid. The material has a molecular weight GPC Mw=20000 Da and glass transition temperature Tg of between 45° C. and 48° C. and melting temperature Tm=160° C.

EXAMPLE 6

To a 2 L five-neck glass jacketed reactor (mechanical stirring, downpipe, thermometer, nitrogen inlet and neck for adding reagents) are added 200 g D-lactide, 800 g Dimethicone bis-hydroxyterminated (Baysilone OF OH 702 E, Momentive Performance Materials, Inc.) and 0.05 g zinc(II) 2-ethylhexanoate. After flushing dry nitrogen for one hour, the internal temperature is brought to 140° C. and allowed to react to complete depletion of lactide, controlled by infrared spectroscopy. At the end of the reaction, the internal temperature is brought to 30° C. and a clear fluid is discharged, having a molecular weight GPC Mw=3000 Da, Brookfield viscosity v=12000 cP and density d=1.05 g/cm3 at 25° C.

EXAMPLE 7

To a 2 L five-neck glass jacketed reactor (mechanical stirring, downpipe, thermometer, nitrogen inlet and neck for adding reagents) are added 300 g DL-lactide (meso-lactide), 700 g of polyfunctional silicone carbinol (Silmer OH C50, Siltech Corporation) and 0.1 g zinc(II)lactate. After flushing dry nitrogen for one hour, the internal temperature is brought to 140° C. and allowed to react to complete depletion of lactide, controlled by infrared spectroscopy. At the end of the reaction, the internal temperature is brought to 30° C. and a clear fluid is discharged, having a molecular weight GPC Mw=2500 Da, Brookfield viscosity v=6000 cP and density d=1.03 g/cm3 at 25° C.

EXAMPLE 8

To a 2 L five-neck glass jacketed reactor (mechanical stirring, downpipe, thermometer, nitrogen inlet and neck for adding reagents) are added 500 g L-lactide, 500 g of monofunctional silicone carbinol (MCR-C18, Gelest, Inc.) and 0.30 g zinc(II)stearate. After flushing dry nitrogen for one hour, the internal temperature is brought to 160° C. and allowed to react to complete depletion of lactide, controlled by infrared spectroscopy. At the end of the reaction, the temperature is lowered to 80° C. and a translucent fluid is discharged that at room temperature takes the consistency of a white viscous paste. The material has a molecular weight GPC Mw=5500 Da, Brookfield viscosity v=170000 cP at 50° C.

The diplathiconediplathicones, prepared as described above, are characterized by the unique combination of two typical properties of their constituents: like dimethicones, the reduced surface tension facilitates the spreading thereof while they show a typical adhesion in more polar systems, such as polyesters.

A first application of diplathiconediplathicones is that of single binding phase in powdered cosmetic products. Compact powders in which diplathicone LV is present have a good flowability and a silky texture (Examples 9 and 10). In the specific case of compact powder eye shadows (Example 10), a texture is obtained that is just as interesting and creamy, combined with long hold, tested by a panel of 10 volunteers. Moreover in the drop test, which is carried out to evaluate the cohesive properties of a binder, the pieces show high values, well above the limit of acceptability.

In a second application, mixtures of diplathiconediplathicones with different molecular weights and viscosities allow to formulate a lip balm (Example 14) with excellent spreadability, whereby a uniform film with high gloss and good coverage can be applied to the lips.

The diplathiconediplathicones can be used not only as oils but also as functional ingredients in cosmetic formulations. Due to their block structure, they can act as compatibilizing agent between esters and silicones in anhydrous products. In fact, in a third application (Example 15), the diplathiconediplathicones can be added to cosmetic formulations of lipstick with a high content of silicone and esters.

The resulting cosmetic products have no incompatibility phenomena, such as unmixing or seeping, phenomena that usually occur when there is an incompatibility between wax and oil or between different oils. Moreover, the stick lip product (Example 15), where diplathicone MV is present, shows greater brilliancy than the product in which the diplathicone is absent. Finally, an increase in the concentration of diplathicone MV (Example 16) within the formulation of the lipstick greatly improves the cosmetic performances of hold and adherence thereof; maintaining a high ease of application.

Likewise, diplathiconediplathicones are able to effectively disperse a waxy phase as in the following fourth application (Examples 11, 12 and 13). In the examples, the diplathiconediplathicones used stabilize and complex the melted wax. In Example 13, the combination of diplathicone and solidified wax generates a semisolid compound that can be taken with a brush and easy to apply. Properly pigmented, such a material can be used as an anhydrous eyeliner for eye decoration.

A fifth application is the use of diplathiconediplathicones as functional ingredients to impart silicone character to formulations in which it is currently impossible to introduce silicones in high percentage. A salient example are nail polishes (Example 17) where silicones are added in quantities of less than 1% as anti-foaming agents due to the known incompatibility with nitrocellulose and other ingredients known in art and used in such products. The presence of polyester blocks at the ends of the silicone block gives the diplathiconediplathicones compatibility with nitrocellulose, with which it forms hard films having high optical quality (bright and clear).

Diplathicone HV in this application can completely replace traditional resins used in the formulation of polishes. The segregation of silicone blocks to the surface of the film gives the polish a slippery and lubricated surface touch, allowing the creation of innovative textures and improving shine and hold.

EXAMPLE 9

Preparation of a Compact Cosmetic Powder for the Face

| Components | % by weight |
| --- | --- |
| PHASE A | |
| Corn starch | 7.40 |
| Zinc stearate | 0.60 |
| Talc | 77.60 |
| Pigments | 7.00 |
| PHASE B | |
| Preservatives | 0.40 |
| PHASE C | |
| DIPLATHICONE (Example 1) | 7.00 |

The cosmetic powder with the following composition was prepared by mixing phase A with phase B for 5 minutes in a special mill. Phase C is then added and mixed again for 5 minutes. The product thus obtained is sieved and compacted.

EXAMPLE 10

Preparation of a Compact Eye Shadow

| Components | % by weight |
| --- | --- |
| PHASE A | |
| Talc | 40.00 |
| Bead | 40.00 |
| Silica | 4.50 |
| PHASE B | |
| DIPLATHICONE (Example 1) | 7.50 |
| DIPLATHICONE (Example 2) | 7.50 |
| PHASE C | |
| Preservatives | 0.50 |

The following product was obtained by a process of dispersion of powder in a solvent, isododecane. Phase C was dissolved at 45° C. in isododecane, then phase B was added until completely dissolved and finally phase A was added. The mixture thus obtained was homogenized by treatment with a turbine. The resulting dispersion was placed in an oven at 80° C. for 12 h to allow the evaporation of the solvent. The powder obtained after evaporation of the solvent was then sieved and compacted.

EXAMPLE 11

Preparation of a Cream Eye Shadow

| Components | % by weight |
| --- | --- |
| PHASE A | |
| DIPLATHICONE (Example 2) | 18.00 |
| Wax | 2.00 |
| Isododecane | 20.00 |
| Preservatives | 0.20 |
| PHASE B | |
| Beads | 45.00 |
| Silica | 14.80 |

The eye shadow was prepared by dissolving phase A at 95° C., after complete dissolution was added phase B under mechanical stirring and cast into jars.

EXAMPLE 12

Preparation of a Cast Eye Shadow

| Components | % by weight |
| --- | --- |
| PHASE A | |
| Isododecane | 24.50 |
| Synthetic wax | 10.50 |

| Components | % by weight |
| --- | --- |
| Octyldodecanol | 4.00 |
| VP/Eicosene Copolymer | 2.00 |
| VP/Hexadecene Copolymer | 2.00 |
| DIPLATHICONE (Example 3) | 3.50 |
| PHASE B | |
| Pigment | 40.00 |
| Silica | 13.50 |

The cast eye shadow was obtained by dissolving phase A at 95° C., then the powder phase was added under mechanical stirring; the product thus obtained was cast directly into a jar.

EXAMPLE 13

Preparation of an Anhydrous Eyeliner

| Components | % by weight |
| --- | --- |
| PHASE A | |
| Wax | 3.40 |
| DIPLATHICONE (Example 1) | 16.00 |
| DIPLATHICONE (Example 2) | 20.60 |
| Isododecane | 10.00 |
| PHASE B | |
| Pigment | 34.00 |
| Silica | 15.50 |
| PHASE C | |
| Preservatives | 0.50 |

The eyeliner was prepared as in example 12.

EXAMPLE 14

Preparation of a Lip Balm

| Components | % by weight |
| --- | --- |
| PHASE A | |
| DIPLATHICONE (Example 3) | 20.00 |
| DIPLATHICONE (Example 2) | 8.50 |
| DIPLATHICONE (Example 1) | 15.00 |
| PHASE B | |
| Pigment RED7 | 20.00 |
| DIPLATHICONE (Example 1) | 36.50 |

The fluid lip balm was obtained by mixing phase A at 60° C. for 30 minutes. Phase B was laminated at room temperature for about 30 minutes and was added to phase A under mechanical agitation until complete dispersion for additional 30 minutes. The product was then packaged in a bottle with sponge applicator.

EXAMPLE 15

Preparation of a Silicone Lipstick

| Components | % by weight |
|---|---|
| PHASE A | |
| DIPLATHICONE (Example 2) | 6.00 |
| Silicone | 12.00 |
| Triglyceride | 12.00 |
| Wax | 30.00 |
| Butter | 5.00 |
| PHASE B | |
| Pigment RED7 | 20.00 |
| Triglyceride | 15.00 |

The lipstick was obtained by melting phase A at 95° C. and laminating the pigment with the oil phase. Thereafter, phase B was combined with phase A and the two phases were mixed by mechanical stirring. When the mixture became homogeneous, it was cast into special silicone nose-cones, previously heated. The samples were placed on a cooling plate for later extraction of the lipsticks.

EXAMPLE 16

Preparation of a Lipstick

| Components | % by weight |
|---|---|
| PHASE A | |
| DIPLATHICONE (Example 2) | 20.00 |
| Triglyceride | 10.00 |
| Wax | 30.00 |
| Butter | 5.00 |
| PHASE B | |
| Pigment RED7 | 20.00 |
| Triglyceride | 15.00 |

The lipstick was prepared as in Example 15.

EXAMPLE 17

Preparation of a Transparent Polish Base for Nails

| Components | % by weight |
|---|---|
| PHASE A | |
| Solvent | 54.46 |
| Cellulose nitrate | 7.14 |
| PHASE B | |
| DIPLATHICONE (Example 3) | 9.95 |
| Plasticizer | 6.92 |
| Solvent | 5.48 |

| Components | % by weight |
|---|---|
| PHASE C | |
| Solvent | 13.09 |
| Cellulose nitrate | 1.68 |
| Stearalkonium ectorite | 1.28 |

The transparent polish base for nails was prepared by mixing the three phases at room temperature; this base can be easily colored by adding a pigment (e.g. Red7 lacquer).

Advantageously, the biodegradable copolymers described have a very low environmental impact and a wide versatility in cosmetics.

Another advantage is the fact that by varying only the proportions between moles of lactide and silicone initiator, copolymers with different fluidity and with different chemical and physical properties can be obtained.

The invention claimed is:

1. A cosmetic product comprising a biodegradable copolymer of PLA-PDMS-PLA blocks, wherein PLA indicates a polylactic acid block and PDMS indicates a polysiloxane silicone initiator block, the copolymer being obtained by reaction between L or D lactides, a linear or branched silicone initiator with at least one alcoholic functionality in a and w terminal position and a catalyst, the reaction being conducted with a concentration by weight of lactide ranging from 10% to 20% and with a concentration by weight of the at least one silicone initiator ranging from 80% to 90%, wherein the silicone initiator is bis-hydroxyethoxypropyl dimethicone and has a molecular weight greater than 1800 Da, wherein the biodegradable copolymer has a fluid consistency at room temperature with a molecular weight of between 2500 Da and 3500 Da, a Brookfield viscosity of between 250 Cp and 20000 Cp at 25° C. and a density of between 1.03 g/cm$^3$ and 1.06 g/cm$^3$ at 25° C.

2. A cosmetic product comprising a biodegradable copolymer of PLA-PDMS-PLA blocks, wherein PLA indicates a polylactic acid block and PDMS indicates a polysiloxane silicone initiator block, the copolymer being obtained by reaction between L or D lactides, a linear or branched silicone initiator with at least one alcoholic functionality in a and w terminal position and a catalyst, the reaction being conducted with a concentration by weight of lactide ranging from 40% to 60% and with a concentration by weight of the at least one silicone initiator ranging from 60% to 40%, wherein the silicone initiator is bis-hydroxyethoxypropyl dimethicone and has a molecular weight greater than 1800 Da, wherein the biodegradable copolymer has a paste consistency at room temperature with a molecular weight of between 3500 Da and 6500 Da, and a Brookfield viscosity of between 130000 Cp and 190000 Cp at 50° C.

3. The cosmetic product of claim 1, wherein the catalyst is selected from the group consisting zinc lactate, zinc(II) 2-ethylhexanoate, zinc stearate, tin octoate (tin (II)-2-ethylhexanoate) tin alkoxides, 4-(Dimethylamino)pyridine N-heterocyclic carbenes, 1,3-bis-(2,4,6-trimethylphenyl) imidazol-2-ylidene_N-heterocyclic carbenes, 1,3-bis-(2,4,6-trimethylphenyl)imidazolinium chloride, and Na salt of 2,6-di-tert-butyl-4-methylphenol.

4. A cosmetic composition comprising at least one of the following biodegradable PLA-PDMS-PLA block copolymers, wherein PLA indicates a polylactic acid block and PDMS indicates a polysiloxane silicone initiator block consisting of bis-hydroxyterminated dimethicone having a molecular weight Mw greater than 1800 Da:
   a) a copolymer having a fluid consistency at room temperature, with a molecular weight of between 2500 Da and 3500 Da, a Brookfield viscosity of between 250 cP and 20000 cP at 25° C. and a density of between 1.02 g/cm$^2$ and 1.06 cm$^2$ at 25° C., obtained by reacting a lactide in a concentration of 10% to 20% with a silicone initiator at a concentration of 80% to 90% by weight in the presence of a catalyst;
   b) a copolymer having a paste consistency at room temperature, with a molecular weight of between 3500 Da and 6500 Da, a Brookfield viscosity of between 130000 cP and 190000 cP at 50° C., obtained by reacting a lactide in a concentration of 40% to 60% by weight with a silicone initiator at a concentration of 60% to 40% by weight in the presence of a catalyst.

5. The cosmetic composition of claim 4, wherein the lactide is L-lactide.

6. Cosmetic composition of claim 4, wherein the lactide is D-lactide.

7. The cosmetic composition of claim 4, wherein the bis-hydroxyterminated dimethicone is bis-hydroxyethoxypropyl dimethicone.

8. The cosmetic composition of claim 4, wherein the catalyst is selected from the group consisting zinc lactate, zinc(II)2-ethylhexanoate, zinc stearate, tin octoate (tin (II)-2-ethylhexanoate) tin alkoxides, 4-(Dimethylamino)pyridine N-heterocyclic carbenes, 1,3-bis-(2,4,6-trimethylphenyl)imidazol-2-ylidene_N-heterocyclic carbenes, 1,3-bis-(2,4,6-trimethylphenyl)imidazolinium chloride, and Na salt of 2,6-di-tert-butyl-4-methylphenol.

9. The cosmetic product of claim 2, wherein the catalyst is selected from the group consisting of zinc lactate, zinc (II)2-ethylhexanoate, zinc stearate, tin octoate (tin (II)-2-ethylhexanoate) tin alkoxides, 4-(Dimethylamino)pyridine N-heterocyclic carbenes, 1,3-bis-(2,4,6-trimethylphenyl)imidazol-2-ylidene_N-heterocyclic carbenes, 1,3-bis-(2,4,6-trimethylphenyl)imidazolinium chloride, and Na salt of 2,6-di-tert-butyl-4-methylphenol.

* * * * *